United States Patent [19]

Okushima et al.

[11] Patent Number: 4,971,968
[45] Date of Patent: Nov. 20, 1990

[54] PYRIDAZINONE DERIVATIVES AND SALTS THEREOF

[75] Inventors: Hiromi Okushima, Kawasaki; Akihiro Narimatsu, Yokohama; Makio Kobayashi, Machida; Isao Shimooda; Yoshimi Kitada, both of Yokohama, all of Japan

[73] Assignee: Mitsubishi Kasei Corporation, Tokyo, Japan

[21] Appl. No.: 679,056

[22] Filed: Dec. 6, 1984

[30] Foreign Application Priority Data

Dec. 14, 1983 [JP] Japan ................. 58-235480

[51] Int. Cl.$^5$ ................. C07D 401/12; C07D 403/12; A61K 31/53; A61K 31/50
[52] U.S. Cl. ..................... 514/242; 514/245; 514/248; 514/252; 544/182; 544/198; 544/309; 544/212; 544/235; 544/237; 544/238
[58] Field of Search ............. 544/182, 198, 237, 235; 514/242, 245, 248, 252

[56] References Cited

U.S. PATENT DOCUMENTS

| | | | |
|---|---|---|---|
| 4,353,905 | 10/1982 | Sircar et al. | 544/238 |
| 4,397,854 | 8/1983 | Sircar | 544/239 |
| 4,508,721 | 4/1985 | Hargreaves | 544/238 |
| 4,521,415 | 6/1985 | Katakami et al. | 544/239 |
| 4,521,416 | 6/1985 | Sircar et al. | 544/239 |

OTHER PUBLICATIONS

Steck et al., J. Het., Chem. 11, 755 (1974).

*Primary Examiner*—Mark L. Berch
*Attorney, Agent, or Firm*—Oblon, Spivak, McCelland, Maier & Neustadt

[57] ABSTRACT

There are provided novel pyridazinone derivatives having the general formula (I):

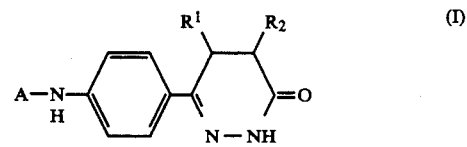

wherein A represents 5- or 6-membered heterocyclic ring having 1-3 nitrogen atoms, which may be substituted by at least one member selected from the group consisting of $C_{1-5}$ alkyl, cyano, hydroxyl, $C_{1-5}$ alkoxyl, amino, $C_{1-5}$ alkylamino, $C_{2-6}$ dialkylamino, $C_{2-5}$ acylamino, carboxyl, $C_{2-5}$ alkoxycarbonyl and carbamoyl, and $R^1$ and $R^2$ independently represent hydrogen atom or $C_{1-5}$ alkyl or $R^1$ and $R^2$ may form together $C_{1-5}$ alkylene, and salts thereof.

10 Claims, No Drawings

PYRIDAZINONE DERIVATIVES AND SALTS THEREOF

BACKGROUND OF THE INVENTION

This invention relates to a novel pyridazinone derivative or a salt thereof which is useful for a cardiac stimulant.

Various cardiac stimulants, which effect a direct enhancement of the cardiac contraction, have been available in the treatment of cardiac insufficiency. However, these cardiac stimulants may have some defects such as follows: (1) their safety margin is extremely small; (2) they may cause arrhythmia; (3) their cardiac stimulating activity is transient; and (4) they may not be suitable for oral administration.

A primary object of the present invention is to provide a novel cardiac compound having a high and sustained activity.

SUMMARY OF THE INVENTION:

In the course of the present inventors' study onto compounds which act as cardiac stimulants with a high and sustained activity, the present invention has been achieved.

The present invention pertains to pyridazinone derivatives having the general formula (I):

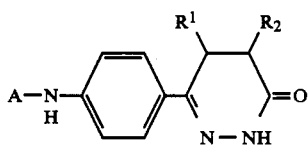

wherein A represents 5- or 6-membered heterocyclic ring having 1-3 nitrogen atoms, the ring being optionally substituted by at least a member selected from the group consisting of $C_{1-5}$ alkyl, cyano, hydroxyl, $C_{1-5}$ alkoxyl, amino, $C_{1-5}$ alkylamino, $C_{2-6}$ dialkylamino, $C_{2-5}$ acylamino, carboxyl, $C_{2-5}$ alkoxycarbonyl and carbamoyl, and $R^1$ and $R^2$ independently represent hydrogen atom or $C_{1-5}$ alkyl or $R^1$ and $R^2$ may form together $C_{1-5}$ alkylene, and salts thereof.

DETAILED DESCRIPTION OF THE INVENTION

The group A in the general formula (I) includes, for instance, pyridyl, pyridazinyl, pyrimidinyl, pyrazinyl, sym-triazinyl, asym-triazinyl, pyrrolyl, imidazolyl, pyrazolyl and the like, which may also be substituted by at least one substituent. By way of illustrating the substituent, mention may be made of normal or branched $C_{1-5}$ alkyl such as methyl, ethyl, propyl, butyl and pentyl; cyano; hydroxyl; normal or branched $C_{1-5}$ alkoxyl such as methoxy, ethoxy, propoxy and butoxy; amino; normal or branched $C_{1-5}$ alkylamino such as methylamino, ethylamino, propylamino and butylamino; normal or branched $C_{2-6}$ dialkylamino such as dimethylamino and diethylamino; normal or branched $C_{2-5}$ acylamino such as acetylamino, propionylamino and butyrylamino; carboxyl; normal or branched $C_{2-5}$ alkoxycarbonyl such as methoxycarbonyl, ethoxycarbonyl, propoxycarbonyl and butoxycarbonyl; and carbamoyl.

Examples of pyridazinone derivatives having the general formula (I) are the following compounds:

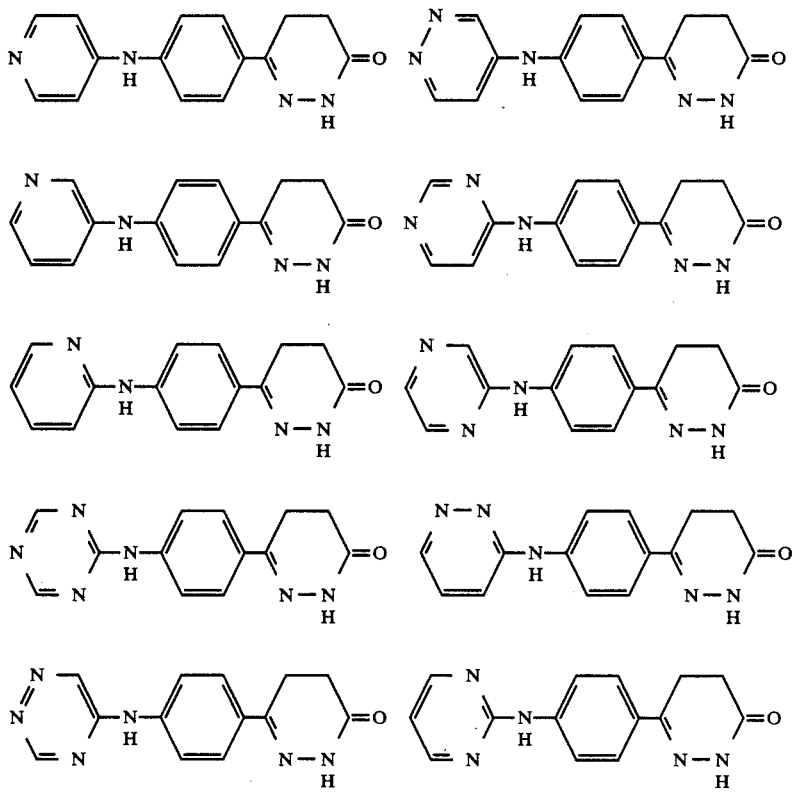

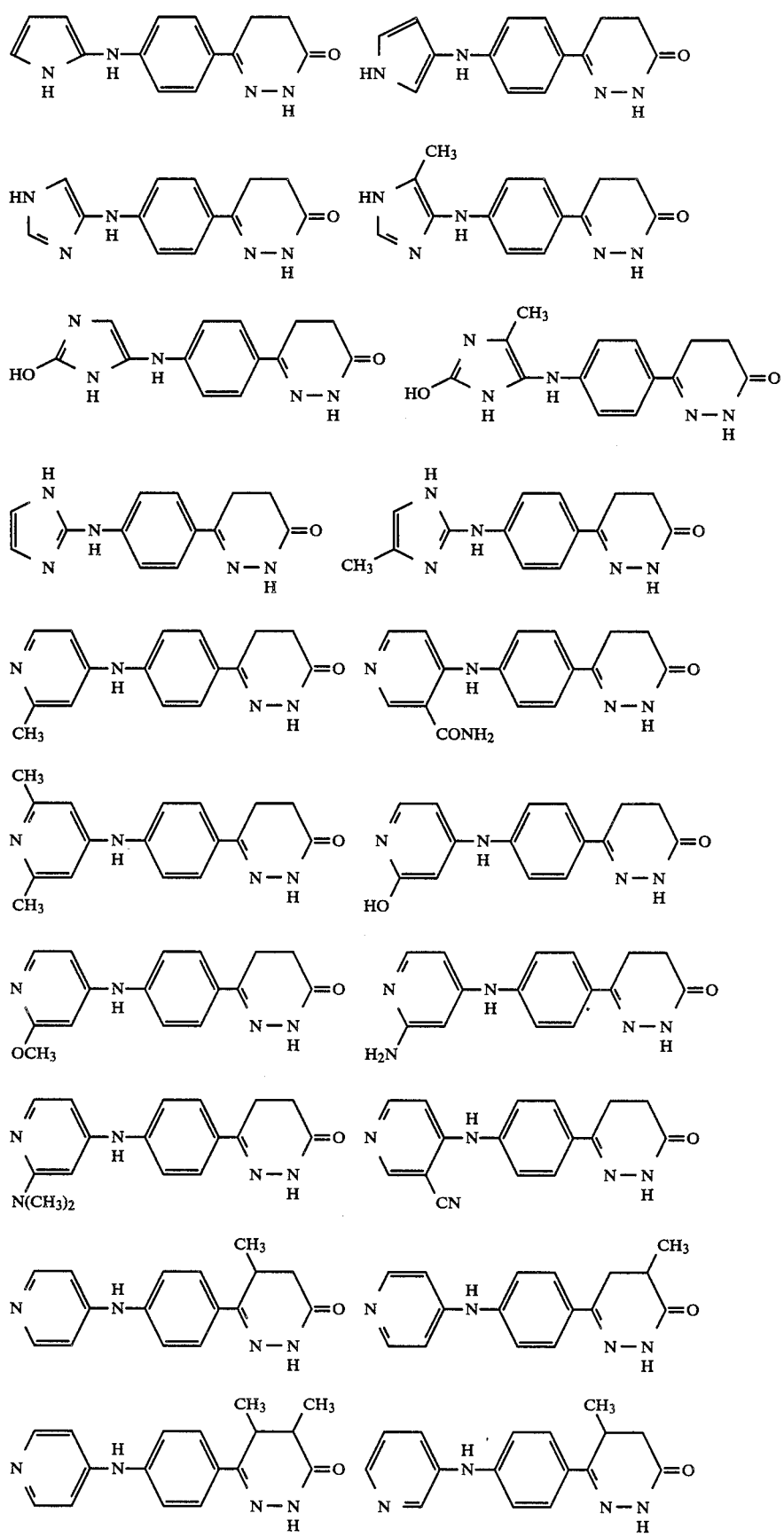

-continued
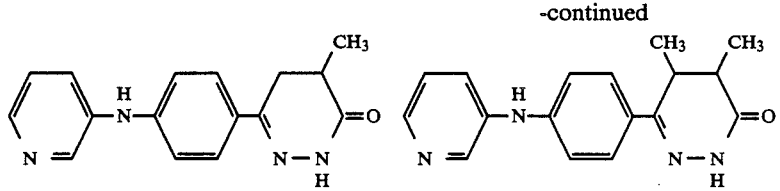
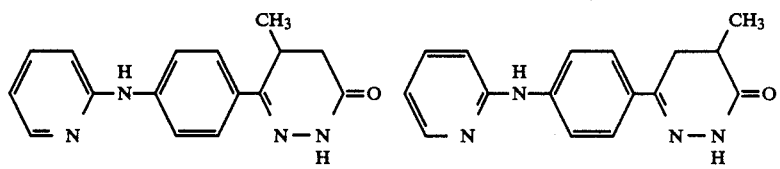
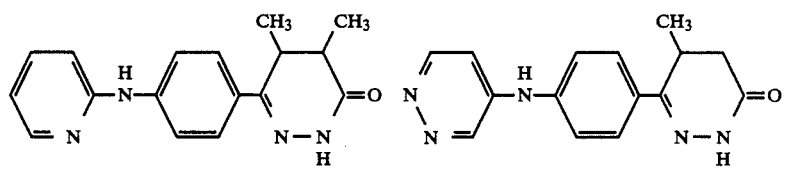
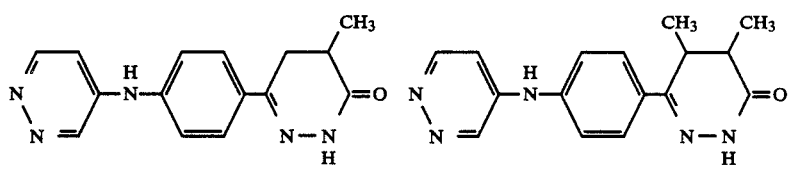
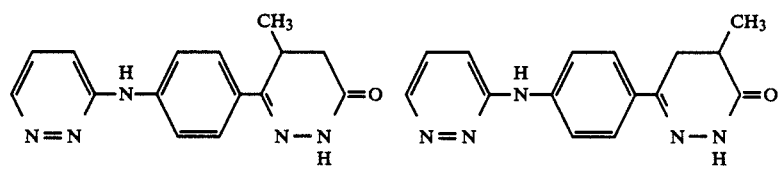
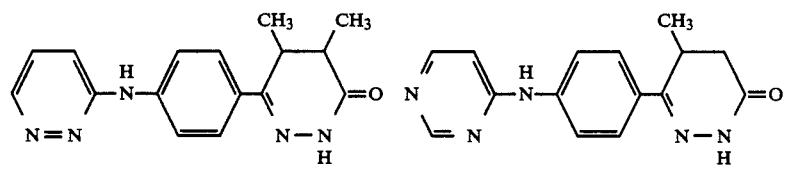
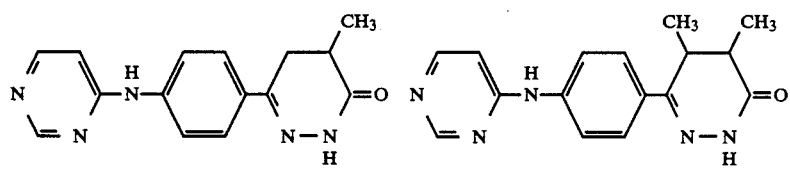
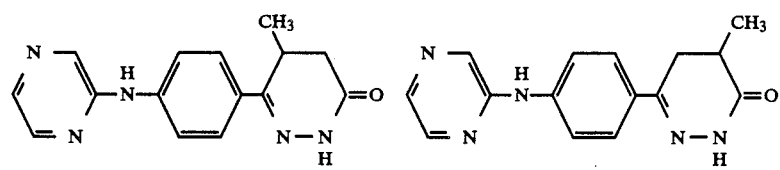
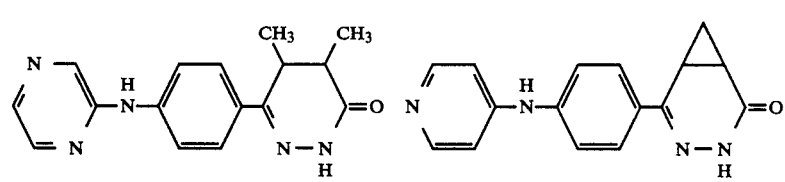

-continued

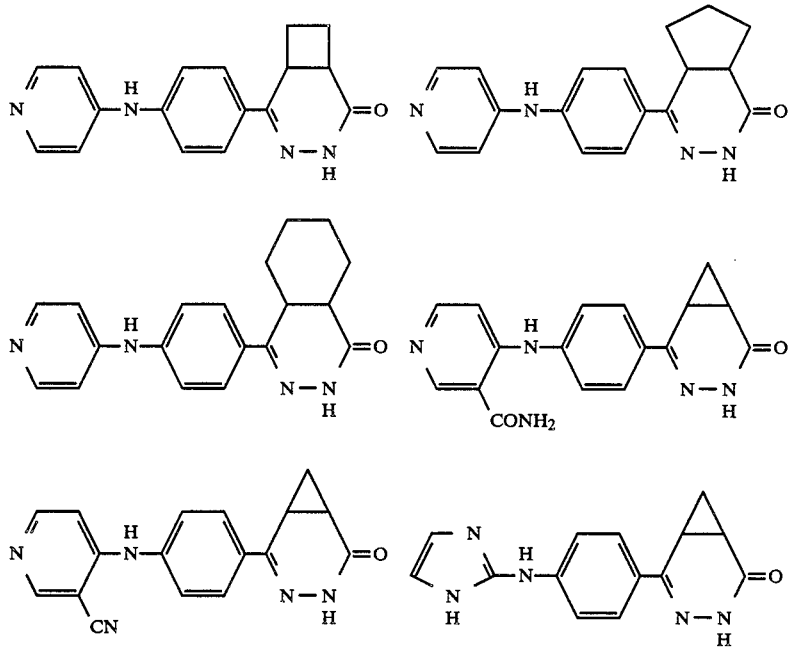

Pharmaceutically acceptable salts of pyridazinone derivatives having the general formula (I) are also included in the scope of the present invention. By illustrating those salts, mention may be made of salts of inorganic acid such as hydrochloric acid and phosphoric acid and of organic acid such as lactic acid and acetic acid. All these compounds are useful as cardiac stimulants.

Preparation of the compound according to the present invention will be described below.

A pyridazinone derivative according to the present invention, for example, may be prepared as follows:

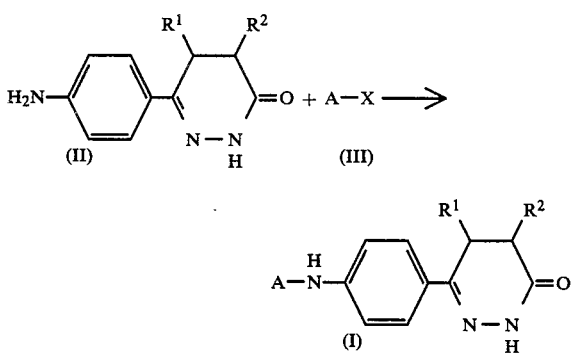

wherein A, $R^1$ and $R^2$ are as defined hereinabove and X represents a halogen atom.

That is, a desired pyridazinone derivative (I) may be synthesized by heating a mixture of a compound (II) and a compound (III) in a polar solvent such as dimethylformamide, dimethylacetamide and phenol at 50°–200° C. for about 0.5–10 hours. A copper compound may be used as a catalyst.

A compound (II) is a known compound described in Journal of Medicinal Chemistry, 17, 273–280 (1974).

The compounds according to the present invention, when used as a cardiac stimulant, may be administered suitably by an oral and parenteral route. By way of illustrating available dosage unit form, mention may be made of powder, granule, tablet, sugar-coated tablet, pill, capsule, solution and the like in case of oral administration, and suppository, suspension, solution, emulsion, ampoule, injectable solution and the like in case of parenteral administration. A combination of these dosage forms may of course be also available. These dosage forms of the compound according to the present invention may be formulated pharmaceutically by the usual way in the art. Dosage can be determined by a physician according to age, sex, body weight, sensitivity to the drug, degree of symptom and physical condition of a patient, administration route, duration and interval of administration, properties, formulation and type of pharmaceutical preparation, kind of active ingredient and so on. Dosage range, for example, is generally 0.01–30 mg/kg/day, and preferably 0.05–10 mg/kg/day by oral administration, but is not restricted by the above.

The invention will be more clearly understood with reference to the following examples, but these examples are not to be construed to limit the scope of the invention.

EXAMPLE I: Preparation of 6-[4-(4'-pyridyl)aminophenyl π-4,5-dihydro-3(2H)-pyridazinone.

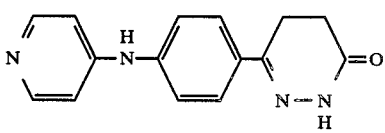

3.89 g of 4-bromopyridine hydrochloride and 3.78 g of 6-(4-aminophenyl)-4,5-dihydro-3(2H)-pyridazinone were dissolved in 50 ml of N,N-dimethylformamide, and then reacted for 2 hours at 105° C. under the nitrogen gas flow. The reaction mixture was poured into 800 ml of water containing 2.12 g of sodium carbonate, and then the deposited crystal was filtered out, washed with water and dried under reduced pressure to recover 4.28 g of 6-[4-(4'-pyridyl)aminophenyl]-4,5-dihydro-3(2H)-pyridazinone in the yield of 70.7%. The crystal thus obtained was dissolved in methyl alcohol with heating, mixed with HCl-ethyl alcohol and then with ether to be converted into hydrochloride salt.

IR(KBr):1642 cm$^{-1}$
MS:M$^{\oplus}$266

EXAMPLE II: Preparation of 6-[4-(2'-pyrimidinyl)aminophenyl] 4,5-dihydro-3(2H)-pyridazinone

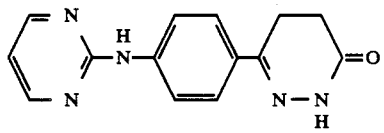

A mixture of 2 g of 6-(4-aminophenyl)-4,5-dihydro-3(2H)-pyridazinone and 1.22 g of 2-chloropyrimidine was heated under reflux in 10 ml of dimethylformamide for 4 hours and cooled to deposit crystal. The deposited crystal was filtered out, washed with dimethylformamide and tetrahydrofuran, and dried to recover 1.20 g of 6-[4-(2'-pyrimidinyl)aminophenyl]-4,5-dihydro-3(2H)-pyridazinone in the yield of 42.5%.

IR(KBr):1670 cm$^{-1}$

Example III: Preparation of 6-[4-(4'-pyridyl)aminophenyl]-4-methyl-4,5-dihydro-3(2H)pyridazinone

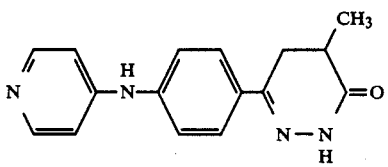

1.02 g of 6-(4-aminophyenyl)-4-methyl-4,5-dihydro-3(2H)-pyridazinone was dissolved in 5 ml of N-methylpyrrolidone, to which 0.35 ml of triethylamine was added and then heated to 90° C. 0.75 g of 4-chloropyridine hydrochloride was added and reacted at 90° C. for 2 hrs. After the reaction mixture was cooled on ice, 50 ml of acetone was added. The deposited crystal was filtered out and dissolved in 50 ml of water. The aqueous solution was adjusted to approximate pH 9 with 1 N NaOH. The deposited crystal was collected by decantation and washed with acetone and n-hexane. Silica gel chromatography of the crystal thus obtained which was dissolved in 10 ml of N,N-dimethylformamide was performed with chloroform/methanol. The fraction of the product was concentrated and dried, and the residue was dissolved in ethanol and mixed with 1N HCl/ethanol to convert into hydrochloride salt. Benzene, hexane, and ethyl acetate were added to the solution to deposit hydrochloride salt which was filtered out and dried to obtain 0.98 g of 6-[4-(4'-pyridyl)aminophenyl]-4-methyl-4,5-dihydro-3(2H)pyridazinone in the yield of 61.6%.

m.p.=241°-244° C.

Example IV: Preparation of 6-[4-(4'-pyridyl)aminophenyl]-5-methyl-4,5-dihydro-3(2H)pyridazinone

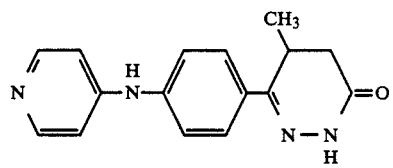

0.81 g of 6-(4-aminophenyl)-5-methyl-4,5-dihydro-3(2H)pyridazinone was dissolved in 4 ml of N-methylpyrrolidone, mixed with 0.28 ml of triethylamine and then heated to 90° C. 0.60 g of 4-chloropyridine hydrochloride was added and reacted at 90° C. for 2 hrs. The reaction mixture was cooled on ice bath and mixed with 50 ml of acetone to deposit crystal. The crystal was dissolved in water and alkalinized with 1N NaOH to deposit the crystal which was then performed silica gel chromatography with chloroform/methanol. The residue which was obtained by the concentration to dryness of the fractions was dissolved in ethyl alcohol and mixed with 1N HCl/ethanol to convert into hydrochloride salt. The ethanol solution was mixed with ether to deposit the crystal which was filtered out and dried to obtain 0.863 g of 6-[4-(4'-pyridyl)aminophenyl]-5-methyl-4,5- dihydro-3(2H)pyridazinone in the yield of 68.3%.

m.p.=249°-252° C.

EXAMPLE V:

Pharmacological and toxicological studies of pyridazinone derivatives according to the present invention were carried out by the following methods to show their utility as a cardiac stimulant.

1. Effect on contraction of an isolated and cross-circulated papillary muscle preparation of the dog An isolated and cross-circulated papillary muscle preparation of the dog was prepared by Endo and Hashimoto's method (referred to American Journal of Physiology, 218, 1459-1463, 1970). The effect of the compound was measured by closely intraarterially injecting the compound dissolved in a solvent to the papillary muscle for the purpose of recording its effect on contraction of papillary muscle. Rate of increase in contraction of papillary muscle is shown in Table 1.

2. Effect on contraction of an isolated left atrium of the guinea pig

A left atrium was isolated from a male guinea pig with 200-300 g of body weight soon after striking on the back of its head. The mitral orifice was fixed to the bottom of an organ bath filled with 30 ml of Krebs-Henseleit solution maintained at 35° C. A gas mixture comprising 95% of $O_2$ and 5% of $CO_2$ was passed through the Krebs-Henseleit solution in the organ bath. Isometric tension was measured by connecting a left auricle of heart and a transducer by a yarn. A resting tension of 0.5 g was given to the atrium, which was then electrically driven with square pulses with duration of 1 msec and voltage of 1.5 times as much as threshold in the rate of 2 Hz via dipolar platinum electrodes.

After stabilizing the atrium for 30 minutes from its preparation, the compound dissolved in a solvent was added to the organ bath to measure its effect. The rate of increase in contraction of left atrium is shown in Table 1.

of Pharmacology and Experimental Therapeutics, 96, 99-113, 1949). The result is shown in Table 1.

TABLE 1

| Compound | Contraction of papillary muscle of dog | | Contraction of left atrium of guinea pig | | Anesthetized dog | | | | $LD_{50}$(mg/kg) | |
|---|---|---|---|---|---|---|---|---|---|---|
| | | | | | | dP/dt max | Cont | CO | | |
| | dosage (μg i.a.) | increase (%) | dosage (g/ml) | increase (%) | dosage (μg/kg i.v.) | increase (%) | increase (%) | increase (%) | i.v. | p.o. |
| Example I (structure) | 10 | 13.2 | $10^{-5}$ | 115 | 10 | 45 | 23 | 13 | 97 | 341 |
| | 30 | 15.4 | $3 \times 10^{-5}$ | 138 | 30 | 93 | 57 | 28 | | |
| Example II (structure) | 30 | 5.7 | $10^{-5}$ | 42 | | | | | | |
| | 100 | 15.9 | $3 \times 10^{-5}$ | 66 | | | | | | |
| Example III (structure) | 10 | 22.6 | $10^{-5}$ | 85.9 | 30 | 29.1 | 21.6 | 8.6 | | |
| | 30 | 50.0 | $3 \times 10^{-5}$ | 109.3 | 100 | 64.7 | 64.0 | 26.7 | | |
| Example IV (structure) | 3 | 28.6 | $10^{-5}$ | 86.6 | 3 | 14.4 | 13.3 | 14.4 | | |
| | 10 | 38.7 | $3 \times 10^{-5}$ | 97.9 | 10 | 73.8 | 75.9 | 26.7 | | |

3. Effects on myocardial contraction in anesthetized dogs

Male and female mongrel dogs with body weight of 8-15 kg were used. A dog was anesthetized by intraveneous injection of 30 mg/kg of sodium pentobarbital and practiced artificial respiration. The dog was thoractomized between fourth and fifth costa which was cut off. The pericardium was incised to expose heart. Blood flow through the aorta, which was measured with an electromagnetic blood flowmeter whose probe was attached to the ascending aorta, was used as an approximate index of cardiac output (CO). Left ventricular pressure (LVP) was measured with a Miller Catheter-tip pressure transducer and the first derivative of the LVP (dP/dt) was measured with a differentiater. Contraction of right ventricular muscle (Cont) was determined with a strain-gauge attached to the wall. Systemic blood pressure was measured from the left femoral artery. Heart rate was measured with electrocardiogram (lead II) and a cardiotachometer. The compound dissolved in a solvent was administered intravenously from a left femoral vein.

Maximum value of dP/dt (dP/dt max) and rate of increase in Cont and CO are shown in Table 1.

4. Acute Toxicity

Acute toxicity ($LD_{50}$) for intravenous and oral administration in male mice was determined by the method of Richfield and Wilcoxon (referred to Journal

What is claimed is:

1. A pyridazinone compound having the formula (I):

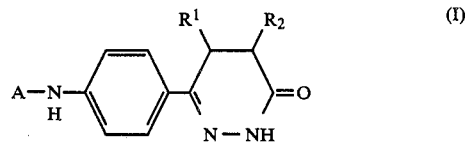

wherein A represents a member selected from the group consisting of pyridyl, pyridazinyl, pyrimidinyl, pyrazinyl, sym-triazinyl, asym-triazinyl, pyrrolyl, imidazolyl and pyrazolyl, A being optionally substituted by at least a member selected form the group consisting of $C_{1-5}$ alkyl, cyano, hydroxyl, $C_{1-5}$ alkoxyl, amino, $C_{1-5}$ alkylamino, $C_{2-6}$ dialkylamino, $C_{2-5}$ acylamino, carboxyl, $C_{2-5}$ alkoxycarbonyl and carbamoyl, and $R^1$ and $R^2$ independently represent hydrogen atom or $C_{1-5}$ alkyl or $R^1$ and $R^2$ may form together $C_{1-5}$ alkylene, and a salt thereof.

2. A pharmaceutical composition useful for cardiac stimulant containing the compound as set forth in claim 1 together with a pharmaceutically acceptable carrier.

3. A method of treating cardiac insufficiency in humans which comprises administering thereto a therapeutically effective amount of the compound as set forth in claim 1, together with a pharmaceutically acceptable carrier.

4. A pyridazinone derivative as set forth in claim 1, wherein A represents an imidazolyl substituted by a methyl and/or a hydroxyl, or a pyridyl substituted by at least a member selected from the group consisting of methyl, cyano, hydroxyl, methoxy, amino, dimethylamino and carbamoyl.

5. A pyridazinone derivative as set forth in claim 1, wherein both $R^1$ and $R^2$ represent hydrogen atom.

6. A pyridazinone derivative as set forth in claim 1, wherein $R^1$ or $R^2$ represents methyl.

7. 6-[4-(4'-pyridyl)aminophenyl]4,5-dihydro-3(2H)-pyridazinone.

8. 6-[4-(2'-pyrimidinyl)aminophenyl]4,5-dihydro(3(2H)-pyridaxinone.

9. 6-[4-(4'-pyridyl)aminophenyl]4-methyl-4,5-dihydro(3(2H)pyridazinone.

10. 6-[4-(4-pyridyl)aminophenyl]5-methyl-4,5-dihydro-(3(2H)pyridazinone. 2H)pyridazinone.

* * * * *